(12) United States Patent
Barthe et al.

(10) Patent No.: US 8,235,909 B2
(45) Date of Patent: Aug. 7, 2012

(54) METHOD AND SYSTEM FOR CONTROLLED SCANNING, IMAGING AND/OR THERAPY

(75) Inventors: Peter G. Barthe, Phoenix, AZ (US); Michael H. Slayton, Tempe, AZ (US)

(73) Assignee: Guided Therapy Systems, L.L.C., Mesa, AZ (US)

( * ) Notice: Subject to any disclaimer, the term of this patent is extended or adjusted under 35 U.S.C. 154(b) by 2079 days.

(21) Appl. No.: 11/126,760

(22) Filed: May 11, 2005

(65) Prior Publication Data

US 2005/0256406 A1 Nov. 17, 2005

Related U.S. Application Data

(60) Provisional application No. 60/570,145, filed on May 12, 2004.

(51) Int. Cl.
*A61B 8/14* (2006.01)
(52) U.S. Cl. .................................... 600/463; 606/130
(58) Field of Classification Search .............. 600/407, 600/411, 424–427, 437, 439, 443–446, 459, 600/461–463; 606/130; 128/916
See application file for complete search history.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |

(Continued)

FOREIGN PATENT DOCUMENTS

DE 4029175 3/1992

(Continued)

OTHER PUBLICATIONS

Notice of Allowance, U.S. Appl. No. 11/163,177; mailed Oct. 9, 2008.
Notice of Allowance, U.S. Appl. No. 10/950,122; mailed Dec. 30, 2008.
Notice of Allowance, U.S. Appl. No. 11/163,155; mailed Jan. 30, 2009.
Notice of Allowance, U.S. Appl. No. 11/380,161; mailed Mar. 30, 2009.

(Continued)

*Primary Examiner* — Brian Casler
*Assistant Examiner* — Saurel J Selkin
(74) *Attorney, Agent, or Firm* — Snell & Wilmer, L.L.P.

(57) ABSTRACT

A method and system for three dimensional scanning, imaging and/or therapy are provided. In accordance with one aspect, an exemplary method and system are configured to facilitate controlled scanning within one-degree of freedom. For example, an exemplary method and system can enable multiple two-dimensional image planes to be collected in a manner to provide an accurate and computationally efficient three-dimensional image reconstruction while providing the user with a user-friendly mechanism for acquiring three-dimensional images. In accordance with an exemplary embodiment, an exemplary scanning and imaging system comprises an imaging probe, a control system, a positioning system and a display system. In accordance with an exemplary embodiment, the positioning system comprises a guide assembly and a position sensing system. The guide assembly is configured to provide pure rectilinear or rotational motion of the probe during scanning operation while the position sensing system is configured to detect the direction and position of the probe during scanning.

24 Claims, 7 Drawing Sheets

U.S. PATENT DOCUMENTS

| | | | |
|---|---|---|---|
| 4,372,296 A | 2/1983 | Fahim | |
| 4,381,007 A | 4/1983 | Doss | |
| 4,381,787 A | 5/1983 | Hottinger | |
| 4,397,314 A | 8/1983 | Vaguine | |
| 4,409,839 A | 10/1983 | Tanezer | |
| 4,441,486 A | 4/1984 | Pounds | |
| 4,452,084 A | 6/1984 | Taenzer | |
| 4,484,569 A | 11/1984 | Driller | |
| 4,513,749 A | 4/1985 | Kino et al. | |
| 4,527,550 A | 7/1985 | Ruggera et al. | |
| 4,528,979 A | 7/1985 | Marchenko | |
| 4,567,895 A | 2/1986 | Putzke | |
| 4,586,512 A | 5/1986 | Do-Huu et al. | |
| 4,601,296 A | 7/1986 | Yerushalmi | |
| 4,646,756 A | 3/1987 | Watmough | |
| 4,663,358 A | 5/1987 | Hyon | |
| 4,668,516 A | 5/1987 | Duraffourd et al. | |
| 4,697,588 A | 10/1987 | Reichenberger | |
| 4,757,820 A | 7/1988 | Itoh | |
| 4,807,633 A | 2/1989 | Fry | |
| 4,858,613 A | 8/1989 | Fry et al. | |
| 4,860,732 A | 8/1989 | Hasegawa et al. | |
| 4,865,041 A | 9/1989 | Hassler | |
| 4,865,042 A | 9/1989 | Umemura | |
| 4,867,169 A | 9/1989 | Machida | |
| 4,874,562 A | 10/1989 | Hyon | |
| 4,875,487 A | 10/1989 | Seppi | |
| 4,893,624 A | 1/1990 | Lele | |
| 4,896,673 A | 1/1990 | Rose | |
| 4,917,096 A | 4/1990 | Englehart et al. | |
| 4,938,216 A | 7/1990 | Lele | |
| 4,938,217 A | 7/1990 | Lele | |
| 4,947,046 A | 8/1990 | Kawabata et al. | |
| 4,951,653 A | 8/1990 | Fry et al. | |
| 4,955,365 A | 9/1990 | Fry et al. | |
| 4,958,626 A | 9/1990 | Nambu | |
| 4,976,709 A | 12/1990 | Sand | |
| 4,979,501 A | 12/1990 | Valchanov | |
| 5,012,797 A | 5/1991 | Liang | |
| 5,036,855 A | 8/1991 | Fry | |
| 5,054,310 A | 10/1991 | Flynn | |
| 5,054,470 A | 10/1991 | Sanghvi et al. | |
| 5,115,814 A | 5/1992 | Griffith | |
| 5,117,832 A | 6/1992 | Sanghvi et al. | |
| 5,123,418 A | 6/1992 | Saurel | |
| 5,143,063 A | 9/1992 | Fellner | |
| 5,143,074 A | 9/1992 | Dory | |
| 5,150,711 A | 9/1992 | Dory | |
| 5,150,714 A | 9/1992 | Green | |
| 5,156,144 A | 10/1992 | Iwasaki et al. | |
| 5,158,536 A | 10/1992 | Sekins | |
| 5,163,421 A | 11/1992 | Bernstein et al. | |
| 5,191,880 A | 3/1993 | McLeod | |
| 5,209,720 A | 5/1993 | Unger | |
| 5,224,467 A | 7/1993 | Oku | |
| 5,230,334 A | 7/1993 | Klopotek | |
| 5,230,338 A | 7/1993 | Allen et al. | |
| 5,265,614 A | 11/1993 | Hayakawa | |
| 5,267,985 A | 12/1993 | Shimada et al. | |
| 5,269,297 A | 12/1993 | Weng et al. | |
| 5,282,797 A | 2/1994 | Chess | |
| 5,295,484 A | 3/1994 | Marcus | |
| 5,304,169 A | 4/1994 | Sand | |
| 5,321,520 A | 6/1994 | Inga et al. | |
| 5,360,268 A | 11/1994 | Hayashi | |
| 5,370,121 A | 12/1994 | Reichenberger et al. | |
| 5,371,483 A | 12/1994 | Bhardwaj | |
| 5,380,280 A | 1/1995 | Peterson | |
| 5,419,327 A | 5/1995 | Rohwedder et al. | |
| 5,435,311 A | 7/1995 | Umemura | |
| 5,458,596 A | 10/1995 | Lax | |
| 5,460,595 A | 10/1995 | Hall et al. | |
| 5,471,988 A | 12/1995 | Fujio et al. | |
| 5,487,388 A * | 1/1996 | Rello et al. ................... 600/445 |
| 5,492,126 A | 2/1996 | Hennige et al. | |
| 5,496,256 A | 3/1996 | Bock | |
| 5,501,655 A | 3/1996 | Rolt et al. | |
| 5,503,320 A | 4/1996 | Webster et al. | |
| 5,507,790 A | 4/1996 | Weiss | |
| 5,520,188 A | 5/1996 | Hennige et al. | |
| 5,522,869 A | 6/1996 | Burdette | |
| 5,524,620 A | 6/1996 | Rosenchein | |
| 5,524,624 A | 6/1996 | Tepper | |
| 5,526,812 A | 6/1996 | Dumoulin et al. | |
| 5,526,814 A | 6/1996 | Cline et al. | |
| 5,526,815 A | 6/1996 | Granz et al. | |
| 5,540,235 A | 7/1996 | Wilson | |
| 5,558,092 A | 9/1996 | Unger | |
| 5,560,362 A | 10/1996 | Sliwa et al. | |
| 5,575,291 A | 11/1996 | Hayakawa | |
| 5,575,807 A | 11/1996 | Faller | |
| 5,577,502 A * | 11/1996 | Darrow et al. ................ 600/426 |
| 5,577,991 A | 11/1996 | Akui et al. | |
| 5,580,575 A | 12/1996 | Unger et al. | |
| 5,601,526 A | 2/1997 | Chapelon et al. | |
| 5,603,323 A | 2/1997 | Pflugrath et al. | |
| 5,609,562 A | 3/1997 | Kaali | |
| 5,615,091 A | 3/1997 | Palatnik | |
| 5,617,858 A | 4/1997 | Taverna et al. | |
| 5,618,275 A | 4/1997 | Bock | |
| 5,620,479 A | 4/1997 | Diederich | |
| 5,638,819 A | 6/1997 | Manwaring et al. | |
| 5,647,373 A | 7/1997 | Paltieli | |
| 5,655,538 A | 8/1997 | Lorraine | |
| 5,657,760 A | 8/1997 | Ying | |
| 5,658,328 A | 8/1997 | Johnson | |
| 5,660,836 A | 8/1997 | Knowlton | |
| 5,665,053 A | 9/1997 | Jacobs | |
| 5,676,692 A | 10/1997 | Sanghvi et al. | |
| 5,685,820 A | 11/1997 | Riek et al. | |
| 5,690,608 A | 11/1997 | Watanabe | |
| 5,694,936 A | 12/1997 | Fujimoto | |
| 5,697,897 A | 12/1997 | Buchholtz | |
| 5,701,900 A | 12/1997 | Shehada et al. | |
| 5,715,823 A | 2/1998 | Wood et al. | |
| 5,720,287 A | 2/1998 | Chapelon et al. | |
| 5,722,411 A | 3/1998 | Suzuki | |
| 5,727,554 A | 3/1998 | Kalend et al. | |
| 5,735,280 A | 4/1998 | Sherman et al. | |
| 5,743,863 A | 4/1998 | Chapelon | |
| 5,746,005 A * | 5/1998 | Steinberg ..................... 33/1 PT |
| 5,748,767 A | 5/1998 | Raab | |
| 5,749,364 A | 5/1998 | Sliwa et al. | |
| 5,755,228 A * | 5/1998 | Wilson et al. ................. 600/459 |
| 5,755,753 A | 5/1998 | Knowlton | |
| 5,762,066 A | 6/1998 | Law et al. | |
| 5,769,790 A | 6/1998 | Watkins | |
| 5,795,297 A * | 8/1998 | Daigle .......................... 600/447 |
| 5,795,311 A | 8/1998 | Wess | |
| 5,810,888 A | 9/1998 | Fenn | |
| 5,817,013 A | 10/1998 | Ginn et al. | |
| 5,817,021 A | 10/1998 | Reichenberger | |
| 5,820,564 A | 10/1998 | Slayton et al. | |
| 5,823,962 A | 10/1998 | Schaetzle | |
| 5,827,204 A | 10/1998 | Grandia et al. | |
| 5,840,032 A | 11/1998 | Hatfield et al. | |
| 5,844,140 A | 12/1998 | Seale | |
| 5,853,367 A | 12/1998 | Chalek et al. | |
| 5,869,751 A | 2/1999 | Bonin | |
| 5,871,524 A | 2/1999 | Knowlton | |
| 5,873,902 A | 2/1999 | Sanghvi et al. | |
| 5,879,303 A | 3/1999 | Averkiou et al. | |
| 5,882,557 A | 3/1999 | Hayakawa | |
| 5,891,034 A | 4/1999 | Bucholz | |
| 5,904,659 A | 5/1999 | Duarte et al. | |
| 5,919,219 A | 7/1999 | Knowlton | |
| 5,924,989 A * | 7/1999 | Polz .............................. 600/443 |
| 5,928,169 A | 7/1999 | Schatzle et al. | |
| 5,931,805 A | 8/1999 | Brisken | |
| 5,938,606 A * | 8/1999 | Bonnefous ................... 600/437 |
| 5,938,612 A | 8/1999 | Kline-Schoder | |
| 5,948,011 A | 9/1999 | Knowlton | |
| 5,957,844 A * | 9/1999 | Dekel et al. .................. 600/439 |
| 5,957,882 A | 9/1999 | Nita et al. | |
| 5,967,980 A * | 10/1999 | Ferre et al. ................... 600/424 |
| 5,968,034 A | 10/1999 | Fulmer | |
| 5,971,949 A | 10/1999 | Levin et al. | |

| | | |
|---|---|---|
| 5,984,882 A | 11/1999 | Rosenchein et al. |
| 5,997,471 A | 12/1999 | Gumb et al. |
| 5,997,497 A | 12/1999 | Nita et al. |
| 6,004,262 A | 12/1999 | Putz et al. |
| 6,007,499 A | 12/1999 | Martin et al. |
| 6,036,646 A * | 3/2000 | Barthe et al. .................. 600/459 |
| 6,039,048 A * | 3/2000 | Silberg ......................... 128/898 |
| 6,042,556 A | 3/2000 | Beach et al. |
| 6,049,159 A | 4/2000 | Barthe et al. |
| 6,050,943 A * | 4/2000 | Slayton et al. ................. 600/439 |
| 6,059,727 A | 5/2000 | Fowlkes |
| 6,071,239 A | 6/2000 | Cribbs et al. |
| 6,080,108 A * | 6/2000 | Dunham ....................... 600/459 |
| 6,086,535 A | 7/2000 | Ishibashi |
| 6,086,580 A | 7/2000 | Mordon et al. |
| 6,090,054 A | 7/2000 | Tagishi et al. |
| 6,093,883 A | 7/2000 | Sanghvi et al. |
| 6,113,558 A | 9/2000 | Rosenchein et al. |
| 6,113,559 A | 9/2000 | Klopotek |
| 6,120,452 A * | 9/2000 | Barthe et al. .................. 600/459 |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura et al. |
| 6,183,426 B1 | 2/2001 | Akisada et al. |
| 6,183,502 B1 | 2/2001 | Takeuchi |
| 6,183,773 B1 | 2/2001 | Anderson |
| 6,190,323 B1 | 2/2001 | Digs |
| 6,190,336 B1 | 2/2001 | Duarte |
| 6,193,658 B1 | 2/2001 | Wendelken et al. |
| 6,210,327 B1 | 4/2001 | Brackett et al. |
| 6,213,948 B1 | 4/2001 | Barthe et al. |
| 6,216,029 B1 | 4/2001 | Paltieli |
| 6,233,476 B1 * | 5/2001 | Strommer et al. ............. 600/424 |
| 6,234,990 B1 | 5/2001 | Rowe et al. |
| 6,241,753 B1 | 6/2001 | Knowlton |
| 6,246,898 B1 * | 6/2001 | Vesely et al. ................... 600/424 |
| 6,273,864 B1 | 8/2001 | Duarte |
| 6,287,257 B1 | 9/2001 | Matichuk |
| 6,296,619 B1 | 10/2001 | Brisken |
| 6,301,989 B1 * | 10/2001 | Brown et al. ............... 74/490.08 |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,769 B1 | 12/2001 | Klopotek |
| 6,325,798 B1 | 12/2001 | Edwards et al. |
| 6,350,276 B1 | 2/2002 | Knowlton |
| 6,356,780 B1 | 3/2002 | Licato et al. |
| 6,361,531 B1 | 3/2002 | Hissong |
| 6,375,672 B1 | 4/2002 | Aksan |
| 6,377,855 B1 | 4/2002 | Knowlton |
| 6,381,497 B1 | 4/2002 | Knowlton |
| 6,381,498 B1 | 4/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,253 B1 | 7/2002 | Koop et al. |
| 6,413,254 B1 | 7/2002 | Hissong et al. |
| 6,419,648 B1 | 7/2002 | Vitek et al. |
| 6,425,865 B1 * | 7/2002 | Salcudean et al. ............. 600/437 |
| 6,425,867 B1 | 7/2002 | Veazy |
| 6,425,912 B1 | 7/2002 | Knowlton |
| 6,428,477 B1 | 8/2002 | Mason |
| 6,428,532 B1 | 8/2002 | Doukas et al. |
| 6,430,446 B1 | 8/2002 | Knowlton |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton et al. |
| 6,440,121 B1 | 8/2002 | Weber |
| 6,443,914 B1 | 9/2002 | Constantino et al. |
| 6,453,202 B1 | 9/2002 | Knowlton |
| 6,461,378 B1 | 10/2002 | Knowlton |
| 6,470,216 B1 | 10/2002 | Knowlton |
| 6,491,657 B2 | 12/2002 | Rowe |
| 6,500,121 B1 | 12/2002 | Slayton et al. |
| 6,500,141 B1 | 12/2002 | Irion et al. |
| 6,508,774 B1 | 1/2003 | Acker |
| 6,511,428 B1 | 1/2003 | Azuma |
| 6,514,244 B2 | 2/2003 | Pope |
| 6,524,250 B1 | 2/2003 | Weber |
| 6,540,679 B2 | 4/2003 | Slayton et al. |
| 6,554,771 B1 * | 4/2003 | Buil et al. ...................... 600/459 |
| 6,569,099 B1 | 5/2003 | Babaev |
| 6,595,934 B1 | 7/2003 | Hissong et al. |
| 6,599,256 B1 | 7/2003 | Acker |
| 6,607,498 B2 | 8/2003 | Eshel |
| 6,623,430 B1 | 9/2003 | Slayton et al. |
| 6,626,854 B2 | 9/2003 | Friedman et al. |
| 6,626,855 B1 | 9/2003 | Weng et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin et al. |
| 6,685,640 B1 | 2/2004 | Fry et al. |
| 6,692,450 B1 | 2/2004 | Coleman et al. |
| 6,699,237 B2 | 3/2004 | Weber |
| 6,719,449 B1 | 4/2004 | Laughlin |
| 6,719,694 B2 | 4/2004 | Weng et al. |
| 6,749,624 B2 | 6/2004 | Knowlton |
| 6,775,404 B1 * | 8/2004 | Pagoulatos et al. ............ 382/154 |
| 6,824,516 B2 * | 11/2004 | Batten et al. ................... 600/439 |
| 6,835,940 B2 | 12/2004 | Morikawa et al. |
| 6,875,176 B2 | 4/2005 | Mourad et al. |
| 6,887,239 B2 | 5/2005 | Elstrom |
| 6,905,466 B2 | 6/2005 | Salgo et al. |
| 6,920,883 B2 | 7/2005 | Bessette |
| 6,921,371 B2 | 7/2005 | Wilson |
| 6,932,771 B2 | 8/2005 | Whitmore |
| 6,936,044 B2 | 8/2005 | McDaniel |
| 6,936,046 B2 | 8/2005 | Hissong |
| 6,948,843 B2 | 9/2005 | Laugharn et al. |
| 6,953,941 B2 | 10/2005 | Nakano et al. |
| 6,958,043 B2 | 10/2005 | Hissong |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba et al. |
| 7,058,440 B2 | 6/2006 | Heuscher et al. |
| 7,063,666 B2 | 6/2006 | Weng et al. |
| 7,070,565 B2 | 7/2006 | Vaezy et al. |
| 7,094,252 B2 | 8/2006 | Koop |
| 7,115,123 B2 | 10/2006 | Knowlton et al. |
| 7,142,905 B2 | 11/2006 | Slayton et al. |
| 7,179,238 B2 | 2/2007 | Hissong |
| 7,189,230 B2 | 3/2007 | Knowlton |
| 7,229,411 B2 | 6/2007 | Slayton et al. |
| 7,235,592 B2 | 6/2007 | Muratoglu |
| 7,258,674 B2 | 8/2007 | Cribbs et al. |
| 7,273,459 B2 | 9/2007 | Desilets |
| 7,297,117 B2 | 11/2007 | Trucco et al. |
| 7,347,855 B2 | 3/2008 | Eshel |
| RE40,403 E | 6/2008 | Cho et al. |
| 7,393,325 B2 | 7/2008 | Barthe et al. |
| 7,398,116 B2 * | 7/2008 | Edwards ........................ 600/424 |
| 7,491,171 B2 | 2/2009 | Barthe et al. |
| 7,615,015 B2 | 11/2009 | Coleman |
| 7,824,348 B2 | 11/2010 | Barthe et al. |
| 8,057,389 B2 | 11/2011 | Barthe et al. |
| 2001/0009997 A1 | 7/2001 | Pope |
| 2001/0014780 A1 | 8/2001 | Martin et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0082528 A1 | 6/2002 | Friedman et al. |

| | | |
|---|---|---|
| 2002/0082589 A1 | 6/2002 | Friedman et al. |
| 2002/0095143 A1 | 7/2002 | Key |
| 2002/0128648 A1 | 9/2002 | Weber |
| 2002/0156400 A1 | 10/2002 | Babaev |
| 2002/0161357 A1 | 10/2002 | Anderson et al. |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193831 A1 | 12/2002 | Smith |
| 2003/0014039 A1* | 1/2003 | Barzell et al. ............... 606/1 |
| 2003/0018255 A1 | 1/2003 | Martin |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0060736 A1 | 3/2003 | Martin et al. |
| 2003/0065313 A1 | 4/2003 | Koop et al. |
| 2003/0074023 A1 | 4/2003 | Kaplan |
| 2003/0083536 A1 | 5/2003 | Eshel et al. |
| 2003/0097071 A1 | 5/2003 | Halmann et al. |
| 2003/0125629 A1 | 7/2003 | Ustuner |
| 2003/0171678 A1* | 9/2003 | Batten et al. ............... 600/443 |
| 2003/0176790 A1 | 9/2003 | Slayton |
| 2003/0191396 A1 | 10/2003 | Sanghvi et al. |
| 2003/0200481 A1 | 10/2003 | Stanley |
| 2003/0212129 A1 | 11/2003 | Liu et al. |
| 2003/0212351 A1 | 11/2003 | Hissong et al. |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton et al. |
| 2004/0015106 A1 | 1/2004 | Coleman |
| 2004/0030227 A1 | 2/2004 | Littrup |
| 2004/0039312 A1 | 2/2004 | Hillstead et al. |
| 2004/0039418 A1 | 2/2004 | Elstrom et al. |
| 2004/0059266 A1 | 3/2004 | Fry et al. |
| 2004/0073079 A1 | 4/2004 | Altshuler et al. |
| 2004/0073113 A1 | 4/2004 | Salgo |
| 2004/0073116 A1 | 4/2004 | Smith |
| 2004/0102697 A1 | 5/2004 | Evron |
| 2004/0143297 A1 | 7/2004 | Ramsey |
| 2004/0152982 A1 | 8/2004 | Hwang et al. |
| 2004/0186535 A1 | 9/2004 | Knowlton et al. |
| 2004/0206365 A1 | 10/2004 | Knowlton |
| 2004/0210214 A1 | 10/2004 | Knowlton |
| 2004/0217675 A1 | 11/2004 | Desilets et al. |
| 2004/0249318 A1 | 12/2004 | Tanaka et al. |
| 2004/0267252 A1 | 12/2004 | Washington |
| 2005/0033201 A1 | 2/2005 | Takahashi et al. |
| 2005/0055073 A1 | 3/2005 | Weber |
| 2005/0070961 A1 | 3/2005 | Maki et al. |
| 2005/0074407 A1 | 4/2005 | Smith |
| 2005/0080469 A1 | 4/2005 | Larson |
| 2005/0113689 A1 | 5/2005 | Gritzky |
| 2005/0137656 A1 | 6/2005 | Malak |
| 2005/0154313 A1 | 7/2005 | Desilets et al. |
| 2005/0154314 A1 | 7/2005 | Quistgaard |
| 2005/0154332 A1 | 7/2005 | Zanelli |
| 2005/0187495 A1 | 8/2005 | Quistgaard et al. |
| 2005/0228281 A1 | 10/2005 | Nefos |
| 2005/0256406 A1 | 11/2005 | Barthe et al. |
| 2005/0261584 A1 | 11/2005 | Eshel |
| 2005/0267454 A1 | 12/2005 | Hissong et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058707 A1 | 3/2006 | Barthe et al. |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton et al. |
| 2006/0074355 A1 | 4/2006 | Slayton et al. |
| 2006/0079816 A1 | 4/2006 | Barthe et al. |
| 2006/0079868 A1 | 4/2006 | Makin et al. |
| 2006/0084891 A1 | 4/2006 | Barthe et al. |
| 2006/0089632 A1 | 4/2006 | Barthe et al. |
| 2006/0089688 A1 | 4/2006 | Panescu |
| 2006/0111744 A1 | 5/2006 | Makin et al. |
| 2006/0116671 A1 | 6/2006 | Slayton et al. |
| 2006/0122508 A1 | 6/2006 | Slayton et al. |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0206105 A1 | 9/2006 | Chopra |
| 2006/0241440 A1 | 10/2006 | Eshel et al. |
| 2006/0241442 A1 | 10/2006 | Barthe et al. |
| 2006/0282691 A1 | 12/2006 | Barthe et al. |
| 2006/0291710 A1 | 12/2006 | Wang et al. |
| 2007/0032784 A1 | 2/2007 | Gliklich et al. |
| 2007/0035201 A1 | 2/2007 | Desilets et al. |
| 2007/0055154 A1 | 3/2007 | Torbati |
| 2007/0055156 A1 | 3/2007 | Desilets et al. |
| 2007/0087060 A1 | 4/2007 | Dietrich |
| 2007/0088346 A1 | 4/2007 | Mirizzi et al. |
| 2007/0167709 A1 | 7/2007 | Slayton et al. |
| 2007/0208253 A1 | 9/2007 | Slayton et al. |
| 2008/0071255 A1 | 3/2008 | Barthe et al. |
| 2008/0086054 A1 | 4/2008 | Slayton et al. |
| 2008/0214966 A1 | 9/2008 | Slayton et al. |
| 2008/0221491 A1 | 9/2008 | Slayton et al. |
| 2008/0275342 A1 | 11/2008 | Barthe et al. |
| 2008/0281237 A1 | 11/2008 | Slayton et al. |
| 2008/0281255 A1 | 11/2008 | Slayton et al. |
| 2008/0294073 A1 | 11/2008 | Barthe et al. |

FOREIGN PATENT DOCUMENTS

| | | |
|---|---|---|
| DE | 10140064 | 3/2003 |
| DE | 10219217 | 11/2003 |
| DE | 20314479 | 3/2004 |
| EP | 0344773 | 12/1989 |
| EP | 1479412 | 11/1991 |
| EP | 0473553 | 4/1992 |
| EP | 0661029 | 7/1995 |
| EP | 1234566 | 8/2002 |
| EP | 1262160 | 12/2002 |
| GB | 2113099 | 8/1983 |
| JP | 3123559 | 5/1991 |
| JP | 03136642 | 6/1991 |
| JP | 4089058 | 3/1992 |
| JP | 7080087 | 3/1995 |
| JP | 7222782 | 8/1995 |
| JP | 2002078764 | 3/2002 |
| JP | 2003050298 | 2/2003 |
| JP | 2003204982 | 7/2003 |
| JP | 2005323213 | 11/2005 |
| KR | 1020010024871 | 3/2001 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | WO9735518 | 10/1997 |
| WO | WO9832379 | 7/1998 |
| WO | WO9933520 | 7/1999 |
| WO | WO9949788 | 10/1999 |
| WO | 0015300 | 3/2000 |
| WO | WO0015300 | 3/2000 |
| WO | WO0021612 | 4/2000 |
| WO | WO0128623 | 4/2001 |
| WO | WO0182777 | 11/2001 |
| WO | WO0182778 | 11/2001 |
| WO | WO0187161 | 11/2001 |
| WO | 0209813 | 2/2002 |
| WO | WO0209813 | 2/2002 |
| WO | WO0224050 | 3/2002 |
| WO | WO02092168 | 11/2002 |
| WO | 03065347 | 8/2003 |

| | | |
|---|---|---|
| WO | WO03070105 | 8/2003 |
| WO | WO03077833 | 9/2003 |
| WO | 03086215 | 10/2003 |
| WO | 03101530 | 12/2003 |
| WO | WO03099177 | 12/2003 |
| WO | 2005090978 | 9/2005 |
| WO | 2006036870 | 4/2006 |
| WO | WO2006042168 | 4/2006 |
| WO | WO2006042201 | 4/2006 |

OTHER PUBLICATIONS

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Mitragotri, Samir; "Healing sound: the use of ultrasound in drug delivery and other therapeutic applications," Nature Reviews; Drug Delivery, pp. 255-260, vol. 4.

Sanghvi, N.T., et al., "Transrectal Ablation of Prostrate Tissue Using Focused Ultrasound," 1993 Ultrasonics Symposium, IEEE, pp. 1207-1210.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Sassen, Sander, "ATI's R520 architecture, the new king of the hill?" http://www.hardwareanalysis.com/content/article/1813, Sep. 16, 2005, 2 pages.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

Chen, L. et al., ""Effect of Blood Perfusion on the ablation of liver perenchyma with high intensity focused ultrasound,"" Phys. Med. Biol; 38:1661-1673; 1993b.

Damianou et al., Application of the Thermal Dose Concept for Predicting the Necrosed Tissue Volume During Ultrasound Surgery, 1993 IEEE Ultrasound Symposium, pp. 1199-1202.

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

Saad et al., "Ultrasound-Enhanced Effects of Adriamycin Against Murine Tumors," Ultrasound in Med. & Biol. vol. 18, No. 8, pp. 715-723 (1992).

Simon et al., "Applications of Lipid-Coated Microbubble Ultrasonic Contrast to Tumor Therapy," Ultrasound in Med. & Biol. vol. 19, No. 2, pp. 123-125 (1993).

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

* cited by examiner

METHOD AND SYSTEM FOR CONTROLLED SCANNING, IMAGING AND/OR THERAPY

CROSS-REFERENCE TO RELATED APPLICATIONS

This application claim priority from U.S. Provisional Application No. 60/570,145, entitled "Method and System for Three-Dimensional Scanning and Imaging" and filed May 12, 2004.

FIELD OF INVENTION

The present invention relates to imaging and treatment systems, and in particular to a method and system for controlled scanning, imaging and/or therapy.

BACKGROUND OF THE INVENTION

Ultrasound images are typically generated and displayed as two-dimensional (2-D) image slices. For example, with reference to FIG. 1A, a conventional ultrasound imaging system 100 comprising a transducer 102 and a control system 104 are configured to obtain two-dimensional imaging information 106 and display two-dimensional imaging slices 108. However, it is often desirable to acquire a whole volume of data in the form of multiple image planes and render it in a three-dimensional (3-D) format, such as for viewing a fetus. Acquiring multiple image slices can be performed by moving the imaging probe in a manner to produce volumetric information. The quality of the computer-rendered 3-D image (the output) is closely related to spatial sampling of the volume-of-interest (the input data). Specifically, for ease and accuracy of the 3-D reconstruction, it would be desirable for the input image planes to be configured a minimum distance apart to avoid spatial aliasing, as well as in a defined attitude and position to avoid gross spatial distortions in rendering based on assumptions about the probe's motion. Unfortunately, prior art methodologies cannot provide such features.

For example, one shortcoming of so-called "free-hand" 3-D scanning is the lack of precision and repeatability in which the 3-D volume is interrogated due to spatially and temporally imprecise angular and linear displacements. As a result a number of pitfalls exist. As a first example, if sensors record the attitude and position of the probe, it is still possible to over- and/or under-sample the volume-of-interest. Second, even if the volume is adequately sampled, the random nature of the input data orientation requires excessive mathematical interpolations to compute a 3-D image in a uniform output grid. Third, if no sensors are used image frame correlation methods cannot accurately ascertain the relative orientation of image planes. Finally, even if six-degree-of-freedom sensors are utilized, such sensors are expensive and have limited range. In fact, what is desirable is motion having a single degree-of-freedom.

Some methodologies have used mechanical fixtures with water baths (for acoustic coupling) as well as motorized assemblies to move an imaging probe in one dimension. However, such mechanisms can be extremely cumbersome and unwieldy for human scanning and may pose safety hazards if designed improperly.

SUMMARY OF THE INVENTION

A method and system for controlled scanning, imaging and/or therapy are provided. In accordance with one aspect, an exemplary method and system are configured to suitably control an imaging probe within a one-degree of freedom. With such control, an exemplary method and system can facilitate three-dimensional imaging. For example, an exemplary method and system can enable multiple two-dimensional image planes to be collected in a manner to provide an accurate and computationally efficient three-dimensional image reconstruction while providing the user with a user-friendly mechanism for acquiring three-dimensional images. In accordance with another aspect of the present invention, an exemplary method and system can allow therapeutic treatment to occur along a prescribed path or pattern. For example, treatments that would normally occur at a single point in space become a line or other guided path after scanning in the controlled pattern, while line treatments scanned along a path can suitably become a matrix of treatments.

In accordance with an exemplary embodiment, an exemplary scanning and imaging system comprises an imaging probe, a control system, a positioning system and a display system. The imaging probe can comprise various probe and/or transducer configurations. For example, the imaging probe can also be configured for a combined imaging/therapy probe, or simply replaced with a therapy probe. The control system and display system can also comprise various configurations for controlling probes and displaying images, including for example a microprocessor with 3-D reconstruction software with a plurality of input/output devices.

In accordance with an exemplary embodiment, a positioning system is configured for facilitating controlled movement of the imaging probe within one-degree of freedom. In accordance with an exemplary embodiment, the positioning system comprises a guide assembly and a position sensing system. The guide assembly is configured to provide pure rectilinear or rotational motion of the probe during scanning operation while the position sensing system is configured to detect the direction of movement and/or position of the probe during scanning.

BRIEF DESCRIPTION OF THE DRAWINGS

The subject matter of the invention is particularly pointed out in the concluding portion of the specification. The invention, however, both as to organization, structure and method of operation, may best be understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to an imaging, therapy and/or scanning system as described herein are merely indicative of exemplary applications for the invention. For example, the principles, features and methods discussed may be applied to any medical application. Further, various aspects of the present invention may be suitably applied to other industrial, manufacturing or engineering applications, such as the inspection of materials such as steel, plastics, concrete or wood. In addition, while various components and devices may be described as coupled together, such coupling can be realized through direct connection of such components and devices, or the coupling together of such components and devices through the interconnection of one or more other components and devices.

In accordance with various aspects of the present invention, a method and system for controlled scanning, imaging and/or therapy are provided. In accordance with one aspect, an exemplary method and system are configured to suitably control an imaging probe within a one-degree of freedom. With such control, an exemplary method and system can facilitate three-dimensional imaging. For example, an exemplary method and system can enable multiple two-dimensional image planes to be collected in a manner to provide an accurate and computationally efficient three-dimensional image reconstruction while providing the user with a user-friendly mechanism for acquiring three-dimensional images.

Figure 2A:
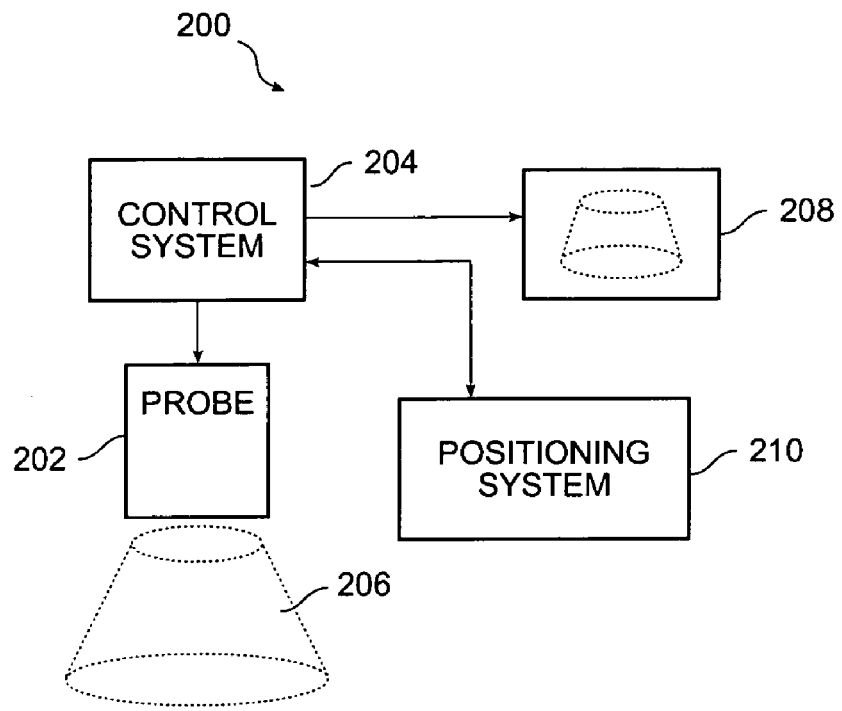
FIG. 2A is a block diagram of an exemplary scanning and imaging system in accordance with an exemplary embodiment of the present invention.

In accordance with an exemplary embodiment, with reference to FIG. 2, an exemplary scanning and imaging system 200 comprises an imaging probe 202, a control system 204, a positioning system 210 and a display system 208.

Imaging probe 202 can comprise various probe and/or transducer configurations. For example, imaging probe 202 can comprise any ultrasound transducer element configured for facilitating imaging of a treatment region. Imaging probe 202 can also comprise any other imaging mechanism, such as lasers, or other light source devices. Imaging probe 202 is configured to obtain 2-dimensional sliced images of a treatment region 206. In addition, imaging probe 202 can comprise other functions. For example, imaging probe 202 can also be configured as a combined imaging and/or therapy probe, a combined imaging and/or therapy and/or temperature monitoring probe, a combined therapy and other tissue parameter monitoring probe, or other combination of tissue parameter monitoring functions. Moreover, imaging probe 202 can be suitably replaced with a therapy-only probe or other single tissue parameter-type probes. Probe 202 can also include those used for applications in urology, such as for bladder volume; obstetrics, such as for fetal viewing; dermatology, such as for forming imaging scan lines and/or therapeutic lesions; and other therapy, and/or imaging/therapy probes such as multi-directional, variable depth, and/or ultra-high frequency probes, as disclosed in U.S. patent application Ser. No. 10/944,499, filed Sep. 16, 2004, in U.S. patent application Ser. No. 10/944,500, filed Sep. 16, 2004 and in U.S. Application No. 60/616,356, filed Oct. 6, 2004, hereby incorporated by reference in their entireties. Imaging, therapy, and/or imaging/therapy probes can be electronic (array-based) or mechanically scanned probes such as those with a direct-drive mechanism and/or linkage mechanism for imaging or treatment in sectors (arcs), lines, or other more complex patterns, e.g. 3-D paths within the probe housing.

Figure 3:
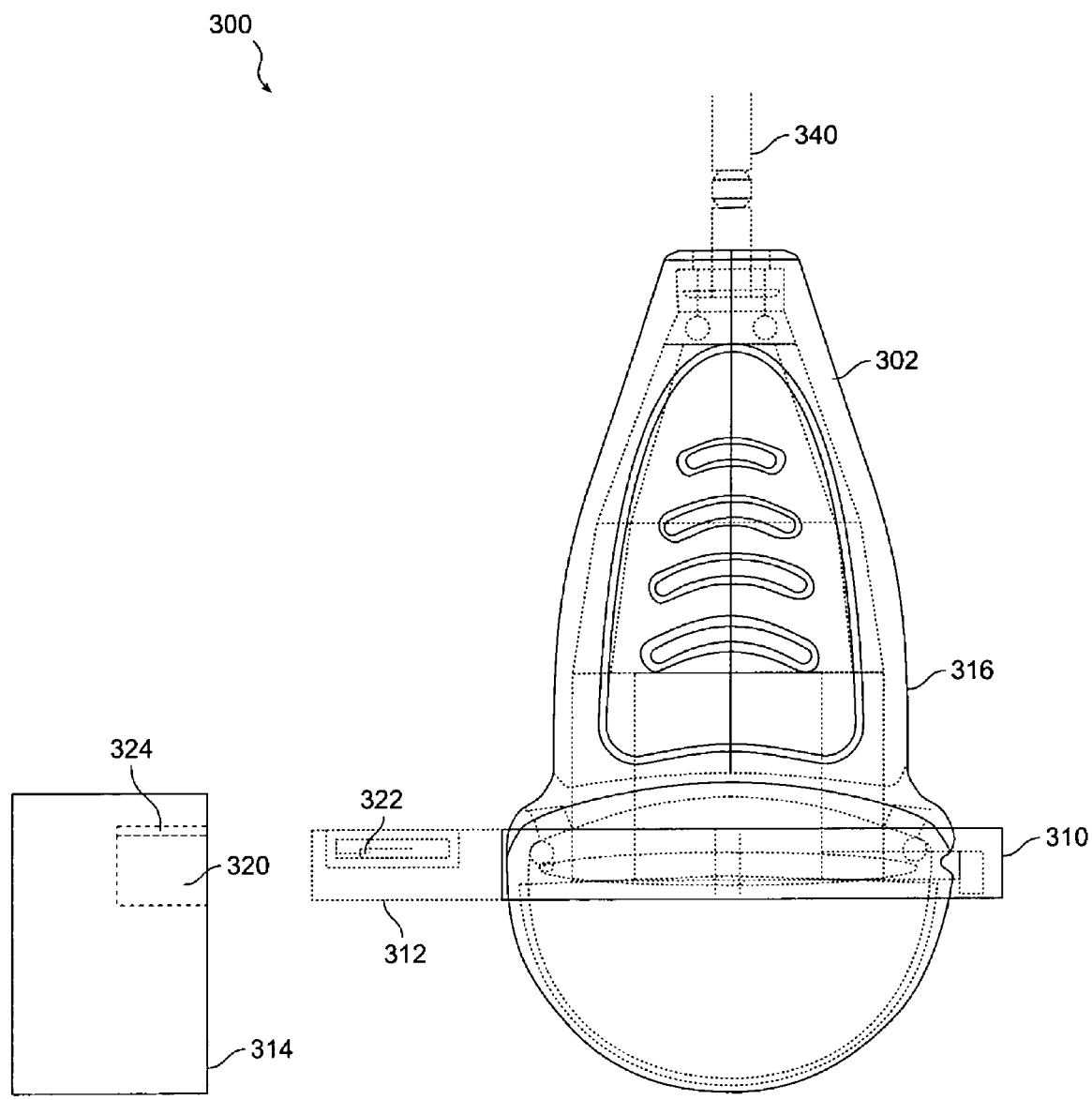
FIG. 3 is a side view of an imaging probe configured with an exemplary guide assembly and a position sensing system for rectilinear motion in accordance with an exemplary embodiment of the present invention.

Imaging probe 202 can also be configured within any housing structure or enclosure, and can be suitably connected to control system 204 in various manners. With momentary reference to an exemplary embodiment illustrated in FIG. 3, an imaging probe 302 can comprise an imaging transducer configured within a housing 316, with a cable 340 configured to couple to a control system.

Control system 204 and display system 208 can also comprise various configurations for controlling probes and displaying images or other information. For example, control system 204 can comprise any conventional microprocessor-based or other computational device. In accordance with an exemplary embodiment, control system 204 comprises a microprocessor with 3-D reconstruction software. Such 3-D software can be configured to interpolate, filter, and/or threshold incoming 2-D image slices, along with positional information, and correlate such information among any other image processing functions to render a 3-D image in a variety of display formats. The 3-D software and/or other resident software may also guide the user with instructions and feedback before, during, and after the 3-dimensional scanning. Control system 204 can also include a plurality of input/output devices. For example, one or more limit switches or other switches, indicators, and/or audible signaling mechanisms to detect or indicate a particular position, e.g., a home position, a user-actuated function, or serve any other function, can be provided. Control system 204 can be communicatively coupled to imaging probe 202, positioning system 210 and display system 208 in any manner now known or hereinafter devised.

Display system 208 is configured to display any portion of the two-dimensional slices, or any other relevant information collected from imaging probe 202, or processed by control system 204. In accordance with an exemplary embodiment, display system 208 is configured to display 3-dimensional images provided by imaging system 200. Display system 208 can comprise any display configuration or device for displaying images and/or information and data. Display system 208 can also be communicatively coupled to control system 204 in any manner, such as by direct cabling, wireless coupling, and/or any combination thereof or any other communication mechanisms.

Figure 1A:
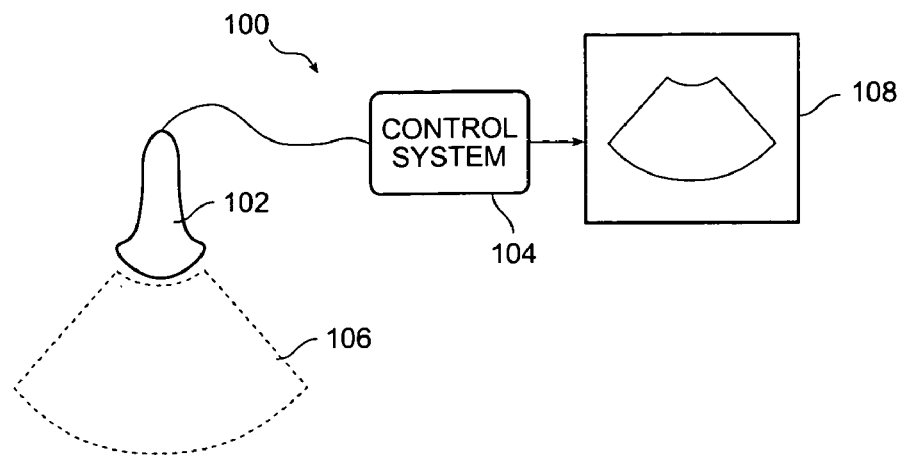
FIG. 1A is a schematic diagram of a 2-D region-of-interest being scanned by a probe connected to a conventional imaging system and display unit, which renders a 2-D image.
Figure 1B:
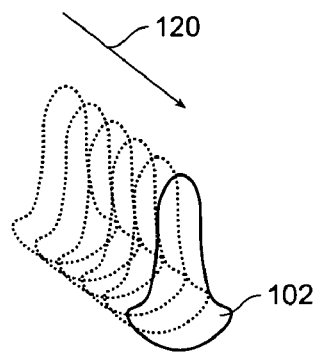
FIG. 1B is a schematic diagram illustrating one-degree-of-freedom rectilinear motion for a probe in accordance with an exemplary embodiment of the present invention.
Figure 1C:
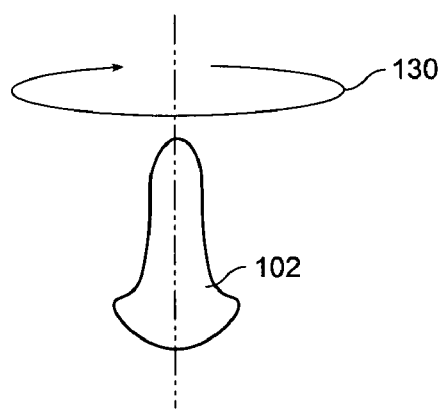
FIG. 1C is a schematic diagram representing one-degree-of-freedom rotational motion of a probe in accordance with an exemplary embodiment of the present invention.

Positioning system 210 is configured for facilitating controlled movement of imaging probe 202 within one-degree of freedom. For purposes of this disclosure, the term "one degree of freedom" comprises any prescribed path or guide such as a straight line, curvilinear line, piecewise linear and/or curvilinear collection of points, axis of rotation and/or combination thereof in two or three dimensions such that a known geometric travel or scan path is achieved. For example, with reference to FIG. 1B, positioning system 210 can be configured to permit substantially rectilinear movement 120 of probe 202, or with reference to FIG. 1C, positioning system 210 can be configured to permit substantially rotational movement 130 of probe 202. Positioning system 210 can also be configured for any other controlled movement within one-degree of freedom, such as, for example, translational movement of probe 202 about treatment region 206, or any other movement comprising curvilinear, piecewise linear and/or curvilinear collection of points, variable axis of rotation and/or combination thereof in two or three dimensions. In addition, positioning system 210 can facilitate manual movement, automated movement, such as by a stepper motor or any other automated movement device, or any combination of manual and automated movement systems. Moreover, while the exemplary embodiment illustrates positioning system 210 configured for control of an imaging probe, positioning system 210 can also be configured for control of movement of a combined imaging/therapy probe, a therapy-only probe, or any other configuration of ultrasound or medical probes.

Figure 2B:
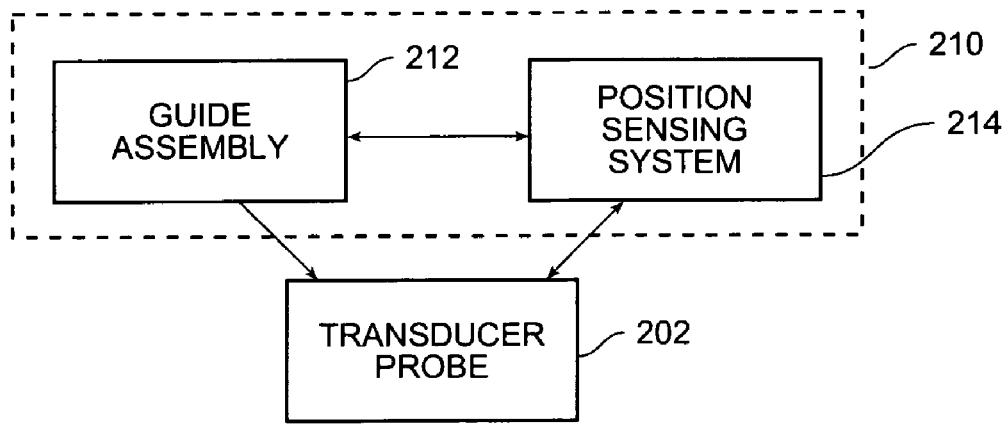
FIG. 2B is a block diagram of an exemplary positioning system configured with an imaging probe in accordance with an exemplary embodiment of the present invention.

In accordance with an exemplary embodiment, with reference to FIG. 2B, positioning system 210 comprises a displacement guide assembly 212 and a position sensing system 214. Displacement guide assembly 212 is configured to provide controlled movement of a probe 202, such as rectilinear, rotational, translational or other controlled motion, with automated and/or manual operation, while position sensing system 214 is configured to detect the direction and position of probe 202 during scanning operation.

Figure 4:
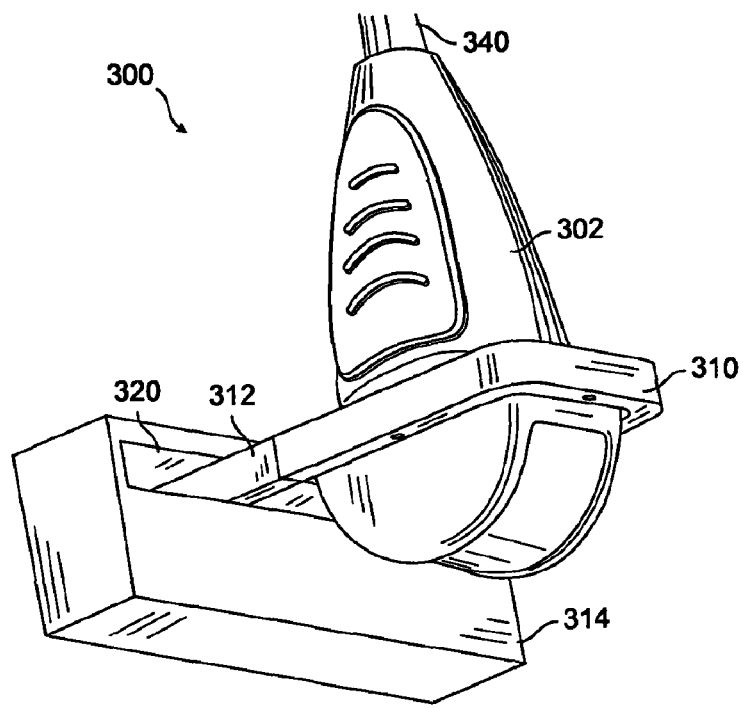
FIG. 4 is an isometric view of the imaging probe configured with an exemplary guide assembly and a position sensing system for rectilinear motion in accordance with an exemplary embodiment of the present invention.

In accordance with an exemplary embodiment, displacement guide assembly 212 can be configured for rectilinear movement. For example, with reference to FIGS. 3 and 4, a guide assembly can comprise a holder device 310 and a stationary guide 314. Holder device 310 is configured to enclose, surround or otherwise attach to probe 302 in a substantially rigid manner, and can comprise various shapes and configurations. In accordance with an exemplary embodiment, holder device 310 comprises a vane-like device that suitably encloses probe 302 on both sides as well as a backside opposite of stationary guide 314, such as for example, a biopsy needle guide configured to geometrically align a biopsy needle; however, holder device 310 can also be configured to enclose on only the sides and/or one side of probe 302, and can be configured in any shape or manner to facilitate a restriction or control of movement of probe 302 relative to stationary guide 314. In addition, holder device 310 can be configured for a quick-engagement and/or attachment to imaging probe 302, such as through a spring clamp or other like device, as well as a more fixed engagement, such as through screw, glue or other more fixed attachments.

Holder device 310 comprises a guide member 312 that can be slidably inserted into a slot 320 of stationary guide 314. Guide member 312 and slot 320 can comprise various sizes, shapes and configurations for allowing slidable insertion to facilitate rectilinear or other like movement. For example, while guide member 312 comprises a square or rectangular configuration in accordance with exemplary embodiment illustrated in FIGS. 3 and 4, guide member 312 can also comprise circular, octagonal, or any other configurations capable of being slidably inserted within slot 320, i.e., guide member 312 does not need to have substantially the same geometric shape or configuration as slot 320, but only capable of being slidably inserted. Guide member 312 can comprise a separate component suitably attached to holder 310 in any manner, or can comprise a unitary member with holder 310, such as comprising a tip-end portion of holder 310. Slot 320 can comprise any slot, raceway, groove or other like guiding path to facilitate and/or restrict the freedom of movement of guide member 312, and thus holder 310 and probe 302, within during scanning operation. The combination and/or insertion of member 312 within slot 320 preclude any angular displacement (e.g., yaw, pitch, or roll) and further allow displacement along only one axis, namely, the axis defined by slot 320. To the extent that slot 320 provides other displacement orientations, e.g., a wave-like pattern, then guide member 312 will suitably follow such other displacement orientations during scanning.

Figure 5:
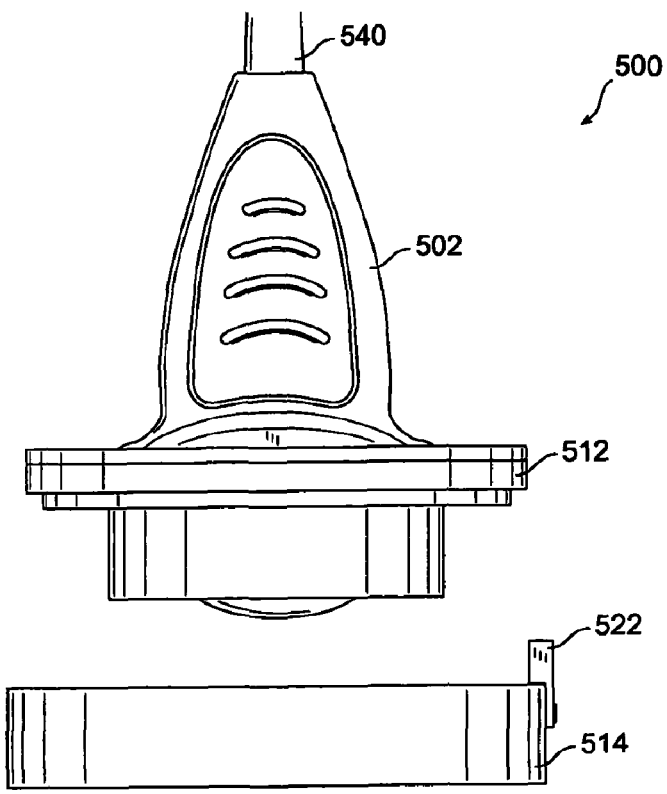
FIG. 5 is an exploded side view of an imaging probe configured with an exemplary guide assembly and a position sensing system for rotational motion in accordance with an exemplary embodiment of the present invention.
Figure 6:
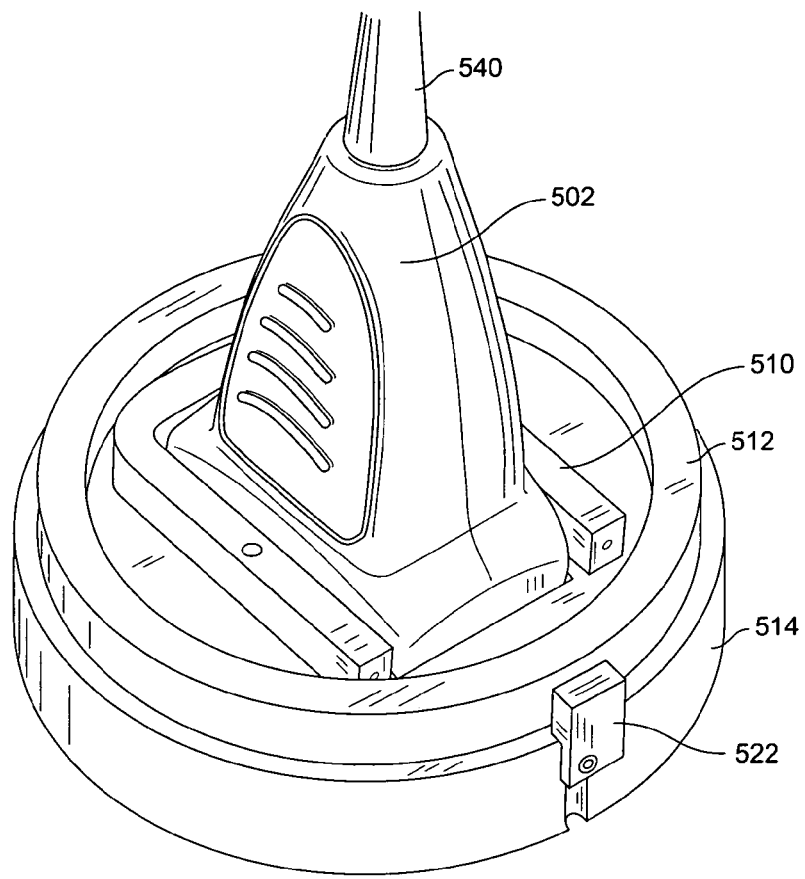
FIG. 6 is an isometric view of an imaging probe configured with an exemplary guide assembly and a position sensing system for rotational motion in accordance with an exemplary embodiment of the present invention.

In accordance with another exemplary embodiment, displacement guide assembly 212 can be configured for rotational movement. For example, with reference to FIGS. 5 and 6, a guide assembly can comprise a rotary device 512 and a stationary guide 514. Rotary device 512 is configured to enclose or surround probe 502, such as probe 502 being configured within a vane member 510 or other holder device configuration and placed within rotary device 512, or probe 502 being configured directly within rotary device 512 without use of vane member 510 or any other holder member. Stationary guide 514 is configured to facilitate controlled rotational movement of rotary device 512. For example, in accordance with an exemplary embodiment, rotary device 512 can comprise essentially one-half of a rotary bearing assembly and stationary guide 514 comprising the other half of a rotary bearing. In accordance with another exemplary embodiment, rotary device 512 and stationary guide 514 can also be configured with a ball bearing arrangement by utilizing a sleeve bearing or assembly such that stationary guide 514 comprises a body of revolution, such as a cylinder, with an inner portion substantially and closely fitting around an outward surface of imaging and/or therapy probe 502.

Figure 8:
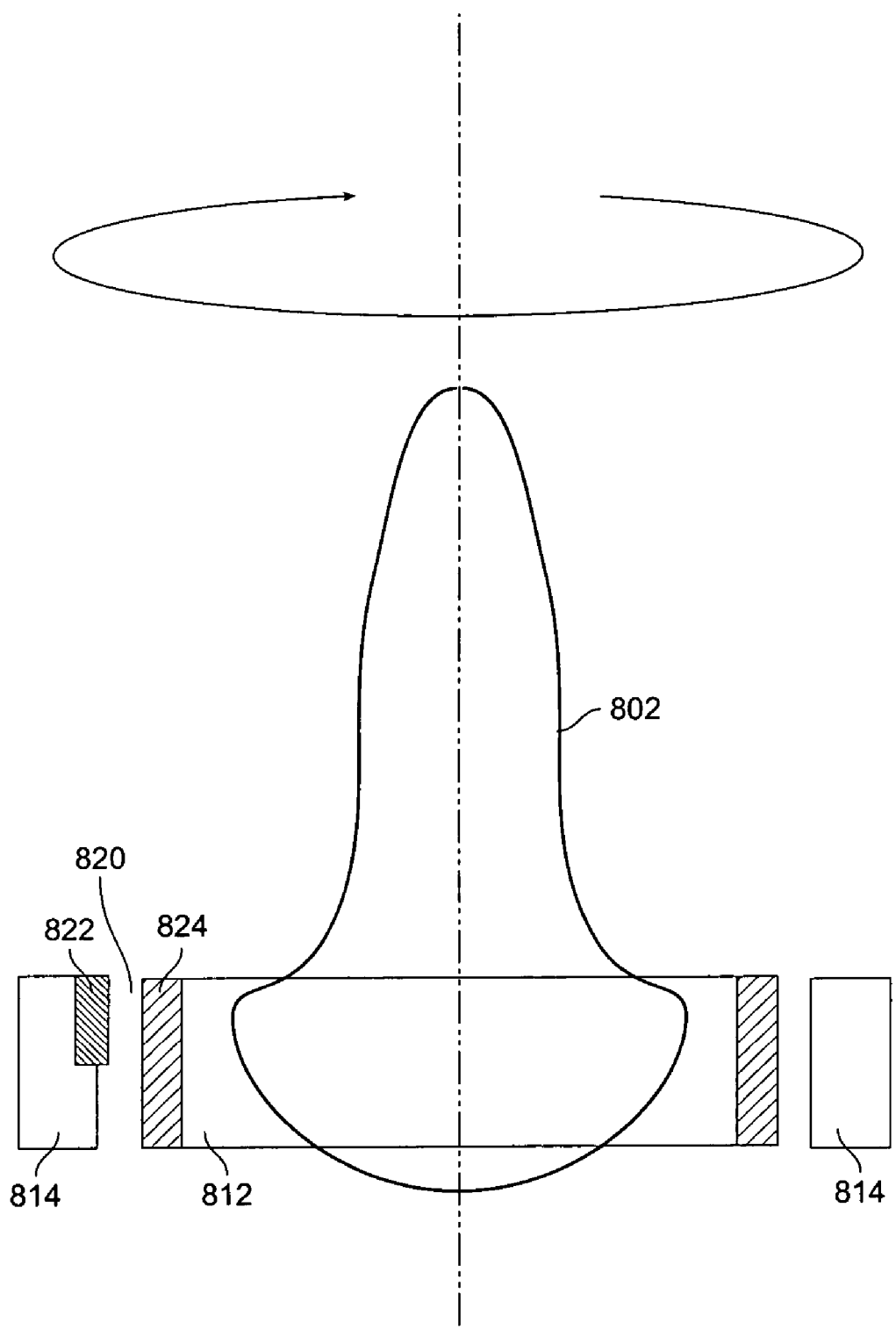
FIG. 8 is a cross-sectional view of a guide assembly for rotational motion in accordance with an exemplary embodiment of the present invention.

In accordance with an exemplary embodiment, rotary device 512 can comprise a guide member and stationary guide 514 comprises a raceway or slot component configured to engage with the guide member of rotary device 512, such as the engagement to permit rotational movement within one-degree of freedom. For example, with momentary reference to FIG. 8, a probe 802 can be configured within a rotary device 812 and defining a slot 820 disposed between rotary device 812 and stationary guide 814. In other words, rotary device 512 can have an outer circumference configured slightly smaller than an inner perimeter of stationary guide 514 such as to permit rotary device 512 to reside within a tight or otherwise restricted fashion as defined by slot 820 to allow rotational movement of rotary device 812 and probe 802 in a controlled manner allowing one-degree of freedom. In accordance with another exemplary embodiment, rotary device can be configured with a guide member that protrudes outward and slidaby engages within a slot or raceway configured within stationary guide 514, such as for example slot 320 within stationary guide 314. Accordingly, rotary device 512 and stationary guide 514 can comprise various sizes, shapes and configurations to facilitate controlled rotational movement of probe 502 about a region of interest.

In accordance with an exemplary embodiment, stationary guide 514 allows rotation of probe 502 along the same central axis, rotating in a single plane; however, rotation can also be permitted in a manner outside the same central axis to maintain spatial control, e.g., in some translational manner. For example, probe 502 can be controllably moved in an arc, i.e. a fixed radius from the center of rotation, such that the probe 502 (or its scan plane) is oriented in a position parallel to the axis of rotation, perpendicular to the axis of rotation, or tilted in a variable orientation with respect to the axis of rotation. Such configurations can be particularly useful in the instance of three dimensional scanning of an annular region of space, while the perpendicular configuration can allow scanning of the inside of a cylinder or cylindrical section, and a tilted probe can allow scanning of a conic section.

While scanning and imaging systems 300 and 500 can be suitably configured to facilitate three-dimensional imaging, in accordance with another aspect of the present invention, an exemplary method and system can also allow therapeutic treatment to occur along a controlled, prescribed path or pattern. For example, therapeutic treatments that would normally occur at a single point in space become a line or other guided path after scanning in the controlled pattern, while line treatments scanned along a path can suitably become a matrix of treatments, while an initial matrix of treatment can become a denser matrix or pattern.

Position sensing system 214 is configured to determine position and/or direction during the controlled rectilinear, rotational and/or translational or other controlled movement. Position sensing system 214 can also provide feedback over time that can also be used to control therapy or imaging functions, such as, for example, the spatial and/or temporal placement of therapeutic lesions, or any other like therapeutic treatment.

For example, in accordance with an exemplary embodiment, with reference again to FIGS. 3 and 4, a position sensing system can comprise a position sensor 322 and an encoder element 324, with position sensor 322 configured within or otherwise coupled to holder device 310, e.g., attached to guide member 312, and configured to interact with encoder element 324 within stationary guide 314 to provide position feedback to a control system during rectilinear movement. In accordance with another exemplary embodiment, position sensor 322 can be integrated inside imaging probe 302 and interfaced to a control system 204. In such a case, encoder element 324 can be placed on stationary guide 314 such that it can be detected by position sensor 322. In accordance with other exemplary embodiments, position sensor 322 can be attached to or configured within stationary guide 314 and encoder element 324 can be attached to or configured within guide member 312, holder device 310 and/or probe 302.

Figure 7:
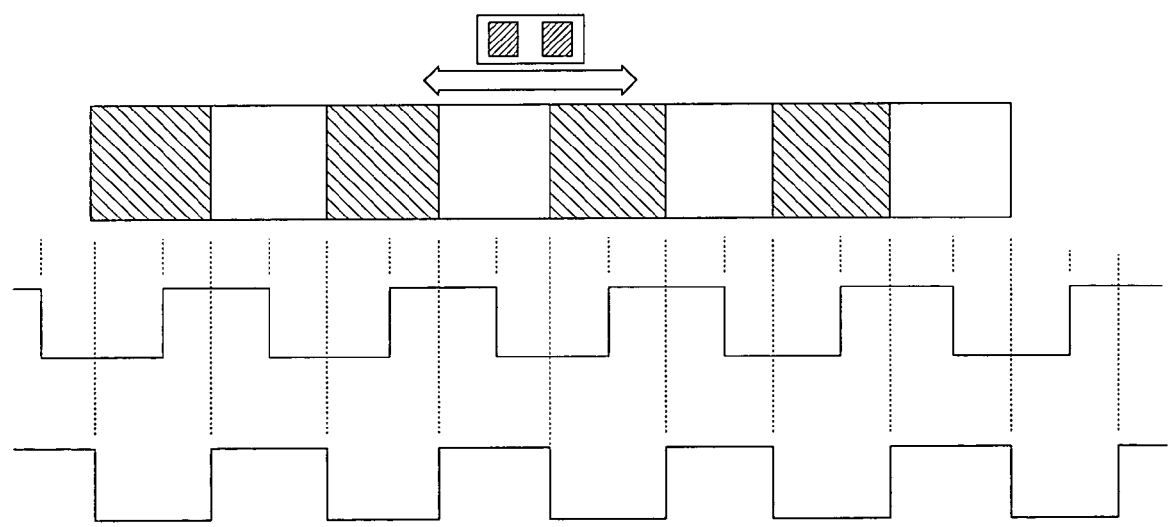
FIG. 7 is a schematic diagram of an output signal for a quadrature position sensor illustrating relative displacement and direction of displacement between an encoder element and a position sensor in accordance with an exemplary embodiment of the present invention.

Position sensor 322 and encoder element 324 can comprise various types of components and configurations. For example, position sensor 322 can comprise a quadrature Hall effect type sensor and encoder element 324 can comprise a multipole flexible magnetic strip, or position sensor 322 can comprise an optical quadrature sensor and encoder strip 324 comprise an alternately optically reflecting and absorbing (opaque) strips configuration. With momentary reference to FIG. 7, a schematic diagram of an output signal for a quadrature position sensor is provided, such as position sensor 322, that outputs quadrature square wave signals that describe the relative displacement and direction of displacement between encoder strip 324 and position sensor 322. Position sensor and encoder can also comprise analog/digital magnetic field sensing integrated circuit(s) and magnetic field producing device(s), such as one or more permanent magnets, whereby rotary, 1-D, 2-D, or 3-D positioning information is derived by measuring magnetic field gradients and field strengths at more than one location on the sensor(s).

In accordance with another exemplary embodiment, with reference again to FIGS. 5 and 6, a position sensing system can comprise a position sensor 522 and an encoder element, with position sensor 522 configured with stationary guide 514 to detect rotational position with the encoder element, e.g., an encoder strip, configured within or coupled to rotary device 512. For example, with momentary reference again to FIG. 8a position sensor 822, such as a magnetic encoder, quadrature magnetic encoder, alternatively optical or other type of sensor device, may be attached to or configured within stationary guide 814 and positioned within or adjacent to slot 820, while rotary device 812 can comprise a linearly encoded magnetic strip 824 or other like encoder device. In accordance with another exemplary embodiment, with reference again to FIG. 5, position sensor 522 can be integrated inside or otherwise coupled to imaging probe 502 and interfaced to a control system. In such a case, an encoder strip is placed on the stationary guide 514 such that it can be detected by position sensor 522.

In addition to a sensor and encoder strips, any other mechanisms for determining position of a first device with respect to a second device can be utilized. For example, the encoder devices and strips can be suitably combined with other encoders having one-degree of freedom, such as to provide a combined two-degree of freedom encoder device, a hemispherical-configured encoder or any other position encoder device. As another example, various limit switches can be configured along the displacement axis that can be suitably enabled by a latch or other enablement device configured with imaging probe 202. In addition, both a limit switch configuration and a sensor/encoder strip configuration can be suitably implemented in accordance with various exemplary embodiments. Moreover, such components can be suitably configured inside and/or alongside imaging probe 202 and displacement guide assembly 212. Still further, the positioning system, including the encoder and/or sensor components, can also be configured in combination with any other positioning device, such as a B-scan arm member or any other positioning devices and components.

Figure 9A:
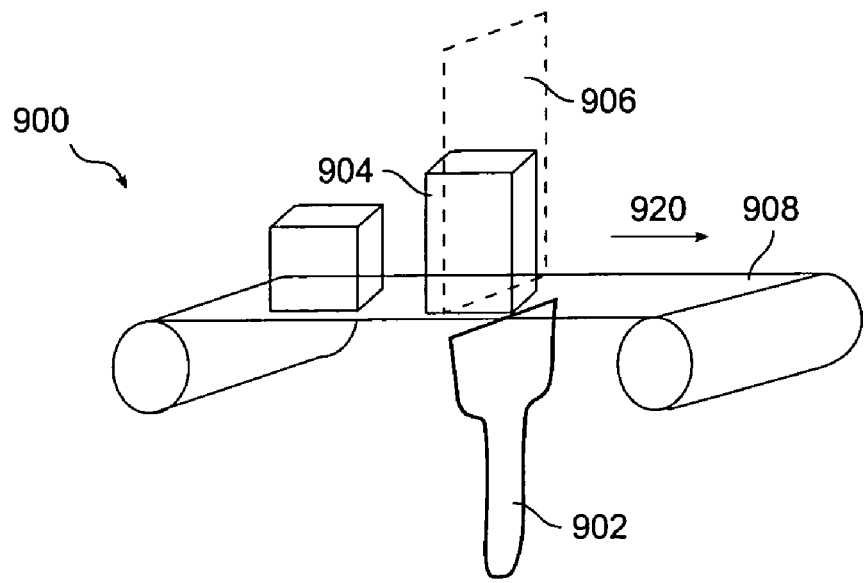
FIG. 9 is a diagram of an exemplary scanning and/or treatment system within a continuous flow arrangement in accordance with an exemplary embodiment of the present invention.

In addition to being configured for controlled movement of probe 202 through use of a guide assembly 212, position sensing system 214 can also be configured for determining position and/or direction of movement where the region of interest is under movement through use of a guide assembly. For example, in accordance with another exemplary embodiment, with reference to FIG. 9A, a scanning, imaging, and/or therapy region of interest 906 may be achieved by moving objects 904 in a direction 920 past a probe 902 through a guide assembly 908 comprising a transport mechanism, such as a conveyor belt or other like arrangement. For example, objects 904 may be mice used in research, or any other desired objects. In this exemplary embodiment, probe 902 is acoustically coupled to object 904 through an acoustically compatible transport mechanism 908. For example, guide assembly 908 comprising a conveyor or other transport mechanism can be made of a thin plastic-like material with low acoustic losses and suitable acoustic impedance, such as TPX plastic or others similar materials. Coupling media such as fluids like water or oils, and/or gels can be suitably utilized.

Figure 9B:
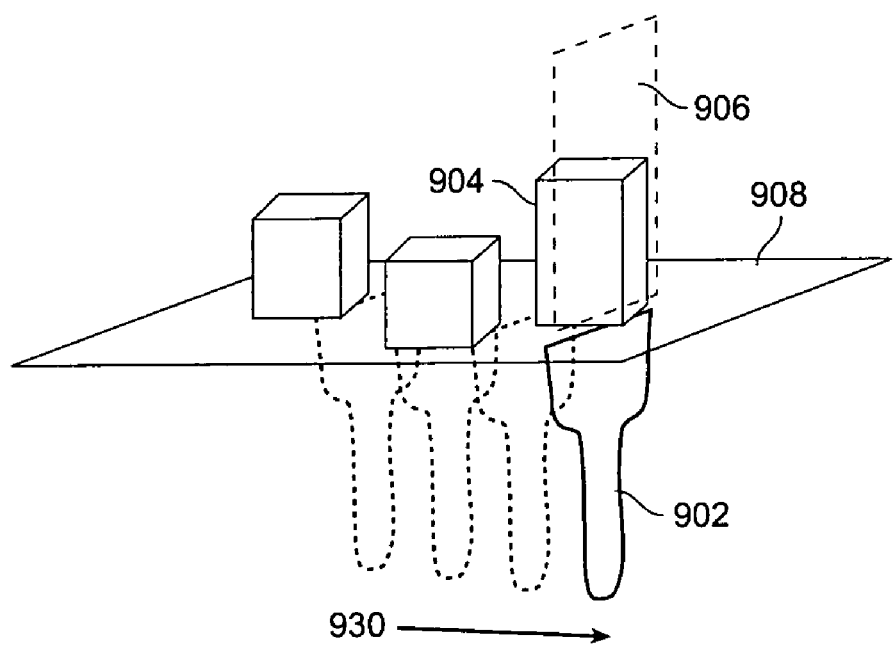

With reference to another exemplary embodiment as shown in FIG. 9B, a single object or collections of objects 904 to be scanned or treated may also lie on and be acoustically coupled to a stationary or nearly stationary surface 918, while probe 902 is swept in a direction 930 utilizing a guide assembly, such as guide assembly 212, past and acoustically coupled to surface 918 to scan objects 904. Surface 918 has the same favorable acoustic characteristics as a guide assembly 908 comprising a moving conveyor, namely an acoustically small thickness, low acoustic losses, and favorable acoustic impedance among others, such as an impedance similar to both objects 904 being scanned and/or treated as well as probe 902. As a result, surface 918 provides efficient transfer of acoustic energy to and from scanned objects 904.

In such rectilinear, rotational or translational configurations, position sensing system 214 can be interfaced to control system 204 via an appropriate communication interface, such as the Universal Serial Bus (USB) or any other available communication interface, such that the position of probe 202, for example, the 2-D image frame position, and/or the direction of movement may be ascertained at any time while image frames are being collected. In addition, the speed of scanning can be determined by control system 204 through detection of position of probe 202 relative to the amount of scanning time, thus enabling a user to prevent under-sampling or under-treatment of volume of interest 206.

The present invention has been described above with reference to various exemplary embodiments. However, those skilled in the art will recognize that changes and modifications may be made to the exemplary embodiments without departing from the scope of the present invention. For example, the various functional components and elements, as well as the components for carrying out the operational thereof, may be implemented in alternate ways depending upon the particular application or in consideration of any number of cost functions associated with the operation of the system. For example, the position encoder and sensor configurations can also be suitably configured for non-imaging applications, such as therapy, temperature monitoring, or any other tissue parameter effect or monitoring. In addition, the various components and devices can comprise numerous types of plastics, metals, woods, composites or other combination of materials thereof to provide the requisite structures or functions. These and other changes or modifications are intended to be included within the scope of the present invention, as set forth in the following claims.

The invention claimed is:

1. A method for facilitating controlled scanning of an imaging probe relative to a region of interest, said method comprising:
   holding an imaging probe in a hand;
   scanning a region of interest with said imaging probe in said hand;
   restricting movement of said imaging probe through use of a guide assembly to rotation around an axis which is substantially perpendicular to a surface of the region of interest; and
   determining position of said imaging probe within said guide assembly through use of a position sensing system to facilitate three-dimensional reconstruction of images by a control system, wherein restricting movement comprises coupling a guide member to said imaging probe.

2. The method according to claim 1, wherein restricting movement comprises controlling movement in a rotational manner.

3. The method according to claim 1, further comprising collecting a plurality of two-dimensional image planes to facilitate said three-dimensional reconstruction of images by a control system.

4. The method according to claim 1, wherein said imaging probe comprises an ultrasound transducer configured with at least one of a single element, multiple element, or electronic array based transducer.

5. The method according to claim 1, wherein said imaging probe is a combined imaging/therapy probe.

6. The method according to claim 5, further comprising placing at least one therapeutic lesion with said combined imaging/therapy probe in said region of interest along said movement of said combined imaging/therapy probe through the use of the guide assembly.

7. The method according to claim 1, further comprising monitoring at least one tissue parameter and reporting to said control system.

8. The method according to claim 1, further comprising providing therapeutic treatment to said region of interest.

9. A method for facilitating controlled scanning of an imaging probe relative to a region of interest, said method comprising:
   holding an imaging probe in a hand;
   scanning a region of interest with said imaging probe in said hand;
   restricting movement of said imaging probe within one-degree, of freedom through use of a guide assembly to rectilinear along a plane which is substantially parallel to a surface of the region of interest; and
   determining position of said imaging probe within said guide assembly through use of a position sensing system to facilitate three-dimensional reconstruction of images by a control system.

10. The method according to claim 9, further comprising collecting a plurality of two-dimensional image planes to facilitate said three-dimensional reconstruction of images by a control system.

11. The method according to claim 9, further comprising coupling the guide member to said imaging probe.

12. The method according to claim 9, wherein said imaging probe comprises an ultrasound transducer configured with at least one of a single element, multiple element, or electronic array based transducer.

13. The method according to claim 9, wherein said imaging probe is a combined imaging/therapy probe.

14. The method according to claim 13, further comprising placing at least one therapeutic lesion with said combined imaging/therapy probe in said region of interest along said movement of said probe through the use of the guide assembly.

15. The method according to claim 9, further comprising monitoring at least one tissue parameter and reporting to said control system.

16. The method according to claim 9, further comprising providing therapeutic treatment to said region of interest.

17. A method for facilitating controlled scanning of an imaging probe relative to a region of interest, said method comprising:
   holding an imaging probe in a hand;
   scanning a region of interest with said imaging probe in said hand;
   restricting movement of said imaging probe within one-degree of freedom through use of a guide assembly to a prescribed path which is substantially parallel to a surface of the region of interest; and
   determining position of said imaging probe within said guide assembly through use of a position sensing system to facilitate three-dimensional reconstruction of images by a control system.

18. The method according to claim 17, further comprising collecting a plurality of two-dimensional image planes to facilitate said three-dimensional reconstruction of images by a control system.

19. The method according to claim 17, further comprising coupling the guide member to said imaging probe.

20. The method according to claim 17, wherein said imaging probe comprises an ultrasound transducer configured with at least one of a single element, multiple element, or electronic array based transducer.

21. The method according to claim 17, wherein said imaging probe is a combined imaging/therapy probe.

22. The method according to claim 21, further comprising placing at least one therapeutic lesion with said combined imaging/therapy probe in said region of interest along said movement of said probe through the use of the guide assembly.

23. The method according to claim 17, further comprising monitoring at least one tissue parameter and reporting to said control system.

24. The method according to claim 17, further comprising providing therapeutic treatment to said region of interest.

* * * * *